United States Patent

Paulsen et al.

[11] 4,218,561
[45] Aug. 19, 1980

[54] PROCESS FOR THE PREPARATION OF GARAMINE AND GARAMINE DERIVATIVES

[75] Inventors: Hans Paulsen; Peter Stadler; Polkhard Iödter, all of Hamburg, Fed. Rep. of Germany

[73] Assignee: Merck Patent Gesellschaft mit beschrankter Haftung, Darmstadt, Fed. Rep. of Germany

[21] Appl. No.: 843,918

[22] Filed: Oct. 20, 1977

[30] Foreign Application Priority Data

Oct. 22, 1976 [DE] Fed. Rep. of Germany ....... 2647807

[51] Int. Cl.$^2$ .............................................. C07H 15/22
[52] U.S. Cl. ..................................... 536/17 R; 536/4; 536/120
[58] Field of Search .......................... 536/17, 13, 4, 120

[56] References Cited

U.S. PATENT DOCUMENTS

| | | | |
|---|---|---|---|
| 4,000,261 | 12/1976 | Daniels | 536/17 |
| 4,063,015 | 12/1977 | Mallams | 536/17 |

Primary Examiner—Johnnie R. Brown
Attorney, Agent, or Firm—Millen & White

[57] ABSTRACT

A process for the preparation of garamine and garamine derivatives of the formula (I)

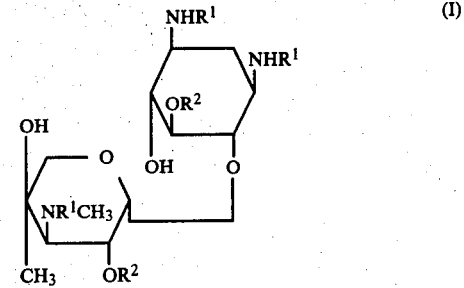

wherein the radicals $R^1$ are each H or amino-protecting groups and the radicals $R^2$ are each H or hydroxyl-protecting groups, comprises selectively cleaving in a strong acid a compound of formula (II) or a mixture thereof

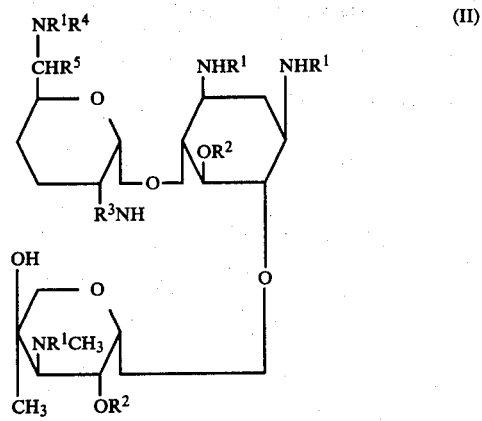

wherein $R^3$ is acyl, $R^4$ and $R^5$ are each H or $CH_3$ and $R^1$ and $R^2$ are the same as in formula (I).

9 Claims, No Drawings

PROCESS FOR THE PREPARATION OF GARAMINE AND GARAMINE DERIVATIVES

BACKGROUND OF THE INVENTION

This invention relates to a new process for the preparation of garamine and garamine derivatives. In particular, it relates to a process for preparing garamine and garamine derivatives whose amino and/or hydroxyl groups are completely or partially protected.

Garamine has hitherto only been preparable by partial hydrolysis of sisomycin. The unsaturated 2,6-diaminosugar unit of sisomycin is split off relatively easily, whereupon the garamine unit is obtained. Generally, penta-N-carbobenzoxy-sisomycin is employed for the hydrolysis. On the other hand, it has been held by the prior art (e.g., J. C. S. Perkin 1976, page 1,088) that garamine cannot be prepared from the clinically important gentamycins $C_1$, $C_2$ and $C_{1a}$ (or from the naturally occurring gentamycin complex, which is a mixture of these substances), since, as a result of the presence of a 2'-amino group, the glycoside bonds of the purpurosamine unit are more stable towards acid hydrolysis.

SUMMARY OF THE INVENTION

Accordingly, it is one object of this invention to provide a new and better process for preparation of garamine, starting from gentamycin.

It has now been found that garamine and garamine derivatives, surprisingly can be obtained by partial cleavage of gentamycins in an acid medium. The gentamycins can be used individually or in the form of the natural complex or mixtures thereof. The starting material gentamycin derivative, at least in the 2'-position, contains an amino group protected by an acyl group. The remaining functional (amino or hydroxyl) groups of the starting material may be protected or unprotected.

More particularly, in a process aspect, the present invention relates to a process for the preparation of garamine and garamine derivatives of the formula (I)

(I)

wherein the radical $R^1$ are each H or amino-protecting groups and the radicals $R^2$ are each H or hydroxyl-protecting groups, by the selective cleavage of at least one compound of the formula (II)

(II)

wherein $R^3$ is an acyl group; $R^4$ and $R^5$ are each H or $CH_3$ and $R^1$ and $R^2$ are as defined above. The cleavage is effected by hydrolysis in strong acids. If desired, any protective groups present in the resulting product can be removed hydrolytically or hydrogenolytically using well-known conventional techniques.

In a composition aspect, the present invention is drawn to new compounds prepared by the process of this invention, e.g., 2',5-di-O-benzyl-tri-N-carbobenzoxy-garamine.

Garamine ($R_1=R_2=H$ in formula (I)) and some of the process products are known, while some products are new. The compounds of formula (I) are valuable intermediate products for the preparation of known and new semi-synthetic aminoglycoside antibiotics, which are related to the clinically important gentamycins.

DETAILED DISCUSSION

The compounds of formula (II) are functional derivatives of saccharide antibiotics which contain the garamine unit. Suitable such starting materials include gentamycin $C_1$, gentamycin $C_2$ and gentamycin $C_{1a}$ as well as the naturally occurring gentamycin complex which is a mixture of these substances and also sagamycin and derivatives thereof which contain, instead of one or more free amino and/or hydroxyl groups, corresponding protected amine and/or protected hydroxyl groups, but wherein the amino group in the 2'-position is always in the acylated form. The starting materials of the formula (II) are essentially known. However, new starting materials of the formula (II) can readily be prepared in analogous manner to that used to prepare the known starting materials. Such methods are conventional and are disclosed in the literature, e.g. J. C. S. Perkin 1976, pages 1078–1146 and the literature cited therein.

In the compounds of the formulae (I) and (II), the radicals $R^1$ are each H or preferably amino-protecting groups. The individual radicals $R^1$ can be the same or different and those which are amino-protecting groups can also be different from one another. However, it is preferred that the amino-protecting groups present be identical.

The expression "amino-protecting group" is quite conventional and refers to groups which are suitable for protecting, i.e., blocking, an amino group from chemical reactions, but which can be removed easily after the desired chemical reaction at other positions of the molecule has been completed. Suitable such groups include unsubstituted or substituted acyl, unsubstituted or substituted aryl (e.g., 2,4-dinitrophenyl) and substituted or unsubstituted aralkyl (e.g., benzyl, 4-nitrobenzyl or triphenylmethyl). Since the amino-protecting groups are removed after the desired reaction (or reaction sequence), their nature and size is in other respects not critical. However, those with 1-20, in particular 1-8, C atoms are preferred. The expression "acyl group" in connection with the present process is to be interpreted in the broadest sense. It encompasses acyl groups derived from aliphatic, araliphatic, aromatic or heterocyclic carboxylic acids or sulphonic acids, and, in particular, alkoxycarbonyl, aryloxycarbonyl and, above all, aralkoxycarbonyl groups. Suitable such acyl groups of this type include alkanoyl, such as acetyl, propionyl or butyryl; aralkanoyl, such as phenylacetyl; aroyl, such as benzoyl or toluyl; alkoxycarbonyl, such as methoxycarbonyl, ethoxycarbonyl, 2,2,2-trichloroethoxycarbonyl, tert-butoxycarbonyl and 2-iodoethoxycarbonyl; and aralkyloxycarbonyl, such as benzyloxycarbonyl ("carbobenzoxy"), 4-methoxybenzyloxycarbonyl and the like. Preferred acyl groups are carbobenzoxy and acetyl. The aryl moiety in all groups mentioned above refers to hydrocarbon aryl groups. Suitable such groups include phenyl and naphthyl. Suitable substituents for all the foregoing groups include chloro, bromo, iodo, nitro and methoxy. Suitable heterocyclic groups include thienyl and benzothienyl. However, all conventional protecting groups are suitable. Conventional protecting groups are disclosed in Accounts of Chemical Research, vol. 6 (1973) pages 191-198 and the literature cited therein.

In the formulae (I) and (II), the radicals $R^2$ are each H or preferably hydroxyl-protecting groups. It is also possible for them to be identical or different from one another. If the radicals $R^2$ are hydroxyl-protecting groups, they are preferably identical; however, they can also be different from one another.

The expression "hydroxyl-protecting group" is also very conventional and relates to groups which are suitable for protecting a hydroxyl group from chemical reactions, but which can be easily removed after the desired chemical reaction at other positions in the molecule has been completed. Suitable such groups include the abovementioned unsubstituted or substituted aryl, aralkyl and acyl groups, and in addition substituted or unsubstituted alkyl groups. The nature and size of the hydroxyl-protecting groups is also not critical, since they are removed after the desired chemical reaction or reaction sequence. However, groups with 1-20, in particular 1-10 C atoms are preferred. Examples of hydroxyl-protecting groups are, inter alia, benzyl, p-nitrobenzoyl, p-toluene-sulphonyl and acetyl; benzyl and acetyl being particularly preferred.

The radical $R^3$ in the compounds of formula (II) is one of the abovementioned acyl groups (in the broad definition). The carbobenzoxy group and, secondarily, the acetyl group are also preferred as $R^3$.

If one or more of the radicals $R^1$ are amino-protective groups, all are preferably the same as the radical $R^3$, in particular carbobenzoxy.

The cleavage of the compounds of formula (II) to produce the compounds of formula (I) is effected with strong acids, preferably trifluoroacetic or perchloric acid. However, any suitable strong acid may be used. Such acids include other strong inorganic acids, such as hydrochloric acid or sulphuric acid, strong organic carboxylic acids, such as trichloroacetic acid, and sulphonic acids, such as benzene- or p-toluene-sulphonic acid. It is possible, but generally not necessary, for an additional inert solvent to be present. Suitable inert solvents are, preferably, organic water-soluble solvents. They include, for example, carboxylic acids, such as acetic acid; ethers, such as tetrahydrofuran or dioxane; ketones, such as acetone; nitriles, such as acetonitrile; alcohols, such as methanol, ethanol or isopropanol. Water may also be used. Mixtures of the abovementioned solvents can also be used. Trifluoroacetic acid is preferably used in excess, without the addition of a further solvent, and perchloric acid is preferably used in the form of a mixture of acetic acid and 70% perchloric acid in a weight ratio of 9:1. A suitable reaction temperature for the cleavage is preferably between about 0° and about 50° C.; the reaction is most preferably carried out between 15° and 30° C. (room temperature) at atmospheric pressure. The concentration of the strong acid for the cleavage reaction ranges from 0.1 to 50 N, preferably from 1 to 15 N. The weight ratio of amount of acid to the amount of compound of formula (II) should be from 1:1 to 30:1, preferably from 3:1 to 20:1. The weight ratio of the amount of solvent to the amount of acid should be from 0:1 to 100:1 preferably 0:1 to 15:1. The reaction is generally carried out to completion, requiring usually from 0.1 to 24 hours, preferably from 0.5 to 10 hours.

The cleavage is preferably carried out in an anhydrous medium or at least in a medium containing a low proportion of water, for example with water contents of less than 5 wt. %, preferably less than 1 wt. %. That is, as noted above, the reaction will proceed in the presence of water, even as a solvent; however, the reaction proceeds advantageously if the amount of water is limited as suggested.

Trifluoroacetic acid is particularly preferred as the cleaving agent; it is preferably employed at room temperature and can be recovered by distillation.

If desired, any protecting groups present in the resulting product can be removed hydrolytically or hydrogenolytically using fully conventional techniques.

Hydrolytic removal of protecting groups, of course, must be carried out under suitably mild conditions, such that the garamine molecule is not deleteriously affected, e.g., so that the ether bonds are not simultaneously split. The hydrolysis is preferably carried out in an alkaline medium.

Protective groups which can be removed hydrogenolytically (e.g., carbobenzoxy or benzyl) can be split off, for example, by treatment with hydrogen in the presence of a catalyst, e.g., a noble metal catalyst, such as palladium, preferably on a support, such as charcoal. Suitable solvents for the hydrogenolysis include alcohols, such as methanol or ethanol. As a rule, the hydrogenolysis is carried out at temperatures between about 0° and 100° C. and under pressures between about 1 and 200 atmospheres, preferably at 20°-30° C. and under 1-10 atmospheres.

Preferred process products have all the amino groups and the two hydroxyl groups in the 2'- and 5-positions protected. These compounds contain only one remaining reactive hydroxyl group, in the 4-position. This makes them suitable as intermediates available for further reactions to produce known classes of antibiotics. For example, these can be reacted with suitably substituted glucopyranosyl halides to give gentamycin analogues (see, for example, German Offenlegungsschrift 2,349,974), such as gentamicin $X_2$, gentamicin B, gentamicin $B_1$, O-2,6-diamino-2,6-dideoxy-α-D-glucopyranosyl-(1→4)-garamine and its 6-C-methyl derivative, antibiotic G-418 and antibiotic JI-33B.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) A solution of 3 g of penta-N-carbobenzoxy-gentamycin (obtainable by adding the benzyl ester of chloroformic acid dropwise to a solution of gentamycin complex in aqueous sodium carbonate solution at 0° C.) in 10 ml of trifluoroacetic acid is allowed to stand for 2.5 hours at 25° C. After evaporation of the solution, the residue is treated twice with 6 ml volumes of toluene and the solution evaporated again. Treatment of the residue with 10 ml of ether followed by renewed evaporation and chromatography on silica gel (elution agent: dichloromethane: methanol, 10:1) yields tri-N-carbobenzoxy-garamine, m.p. 105°–110° C.

The same product can be obtained analogously from penta-N-carbobenzoxy-gentamycin $C_1$, penta-N-carbobenzoxy-gentamycin $C_2$, penta-N-carbobenzoxy-gentamycin $C_{1a}$ or penta-N-carbobenzoxy-sagamycin.

(b) Conventional hydrogenolysis of 2.02 g of tri-N-carbobenzoxy-garamine in 100 ml of methanol on 1 g of 10% Pd-on-charcoal at 25° C. and under 3.4 atmospheres yields garamine, m.p. 89°–99° C.

(c) A solution of 500 mg of tri-N-carbobenzoxy-garamine and 2 g of NaOH in 20 ml of dioxane and 20 ml of water is boiled for 18 hours, cooled and neutralized with Amberlite IRC-50 resin. The resin is washed with water and eluted with 1.5 N ammonia solution. The eluate is evaporated to dryness and chromatographed on silica gel (elution agent: the lower phase of a chloroform/methanol/concentrated ammonium hydroxide (2:1:1) system) to give garamine, m.p. 89°–99° C.

EXAMPLE 2

Analogously to Example 1, di-O-acetyl-penta-N-carbobenzoxy-gentamycin (obtainable by allowing penta-N-carbobenzoxy-gentamycin to stand for 24 hours with acetic anhydride in pyridine at 20° C. and then heating the mixture at 75° C. for 9 hours) and trifluoroacetic acid (reaction time: 1 hour) produces 2′,5-di-O-acetyl-tri-N-carbobenzoxy-garamine, m.p. 107°–112° C.

The same product can be obtained analogously from di-O-acetyl-penta-N-carbobenzoxy-gentamycin $C_1$, di-O-acetyl-penta-N-carbobenzoxy-gentamycin $C_2$, di-O-acetyl-penta-N-carbobenzoxy-gentamycin $C_{1a}$ or di-O-acetyl-penta-N-carbobenzoxy-sagamycin.

EXAMPLE 3

Analogously to Example 1, di-O-benzyl-penta-N-carbobenzoxy-gentamycin (obtainable by stirring 600 mg of penta-N-carbobenzoxy-gentamycin with sodium hydride in dimethylformamide for half an hour at 0° C., adding benzyl bromide dropwise and then stirring the mixture at 0° C. for 3.5 hours) produces 2′,5-di-O-benzyl-tri-N-carbobenzoxy-garamine, m.p. 77°–80° C.

The same product can be obtained analogously from di-O-benzyl-penta-N-carbobenzoxy-gentamycin $C_1$, di-O-benzyl-penta-N-carbobenzoxy-gentamycin $C_2$, di-O-benzyl-penta-N-carbobenzoxy-gentamycin $C_{1a}$ or di-O-benzyl-penta-N-carbobenzoxy-sagamycin.

EXAMPLE 4

A solution of 3 g of penta-N-carbobenzoxy-gentamycin in a mixture of 27 ml of acetic acid and 3 ml of 70% perchloric acid is allowed to stand overnight at 25° C. and further treated analogously to Example 1. This produces tri-N-carbobenzoxy-garamine, m.p. 105°–110° C.

EXAMPLE 5

Analogously to Example 1, penta-N-carbethoxy-gentamycin (obtainable from chloroformic acid ethyl ester and gentamycin complex) yields tri-N-carbethoxy-garamine, m.p. 128°–140° C.

EXAMPLE 6

Analogously to Example 1:
penta-N-acetyl-gentamycin yields:
  tri-N-acetyl-garamine, m.p. 190°–195° C.;
2″,5-di-O-acetyl-penta-N-acetyl-gentamycin yields:
  2′,5-di-O-acetyl-tri-N-acetyl-garamine;
penta-N-acetyl-2″-O-acetyl gentamycin yields:
  tri-N-acetyl-2′-O-acetyl-garamine;
penta-N-(2,4-dinitrophenyl)-gentamycin yields:
  tri-N-(2,4-dinitrophenyl)-garamine, m.p. 192°–205° C.; and
tri-O-acetyl-penta-N-carbobenzoxy-gentamycin yields:
  2′,4′,5-tri-O-acetyl-tri-N-carbobenzoxy-garamine, m.p. 101°–105° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. A process for the preparation of garamine and garamine derivatives of the formula (I)

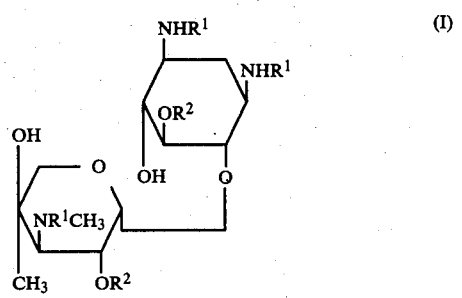

wherein the radical $R^1$ are each H or amino-protecting groups and the radicals $R^2$ are each H or hydroxyl-protecting groups, which comprises selectively cleaving in a strong acid a compound of formula (II) or a mixture thereof

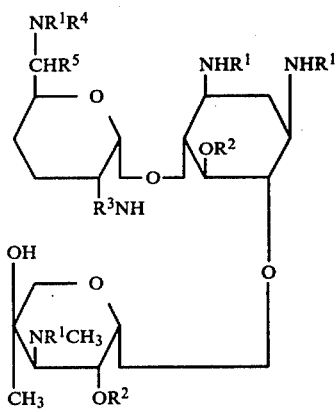 (II)

wherein $R^3$ is acyl, $R^4$ and $R^5$ are each H or $CH_3$ and $R^1$ and $R^2$ are the same as in formula (I).

2. The process of claim 1, which further comprises subsequently removing the protecting groups from the product compound.

3. The process of claim 2, wherein the protecting groups are removed hydrolytically or hydrogenolytically.

4. The process of claim 1, wherein $R^1$ is carbobenzoxy or acetyl.

5. The process of claim 1, wherein $R^2$ is benzyl or acetyl.

6. The process of claim 1, wherein $R^1$ and $R^3$ are the same.

7. The process of claim 6, wherein $R^1$ and $R^3$ are carbobenzoxy.

8. The process of claim 1, wherein the strong acid is trifluoroacetic or perchloric acid.

9. The process of claim 1, wherein the cleavage is conducted at a temperature of 0°–50° C. and in the presence of an inert solvent.

* * * * *